(12) United States Patent
Li

(10) Patent No.: US 10,794,901 B2
(45) Date of Patent: Oct. 6, 2020

(54) QUANTITATIVE LIGANDOMICS FOR SYSTEMATIC IDENTIFICATION OF THERAPEUTIC LIGANDS

(71) Applicant: Wei Li, Miami, FL (US)

(72) Inventor: Wei Li, Miami, FL (US)

(73) Assignee: Wei Li, Miami, FL (US)

( * ) Notice: Subject to any disclaimer, the term of this patent is extended or adjusted under 35 U.S.C. 154(b) by 0 days.

(21) Appl. No.: 15/860,170

(22) Filed: Jan. 2, 2018

(65) Prior Publication Data
US 2019/0204302 A1 Jul. 4, 2019

Related U.S. Application Data

(62) Division of application No. 14/708,073, filed on May 8, 2015, now Pat. No. 10,106,787.

(60) Provisional application No. 61/996,616, filed on May 12, 2014.

(51) Int. Cl.
| | | |
|---|---|---|
| A61P 27/10 | (2006.01) |
| G01N 33/53 | (2006.01) |
| A61P 3/10 | (2006.01) |
| A61P 35/00 | (2006.01) |
| C07K 16/28 | (2006.01) |
| C12Q 1/02 | (2006.01) |
| C12Q 1/68 | (2018.01) |
| G01N 33/15 | (2006.01) |
| C12N 15/09 | (2006.01) |
| A61P 25/28 | (2006.01) |
| C07K 16/18 | (2006.01) |
| G01N 33/68 | (2006.01) |
| C12N 15/10 | (2006.01) |
| A61K 48/00 | (2006.01) |
| A61K 45/00 | (2006.01) |

(52) U.S. Cl.
CPC ............ *G01N 33/53* (2013.01); *A61K 48/00* (2013.01); *A61P 3/10* (2018.01); *A61P 25/28* (2018.01); *A61P 27/10* (2018.01); *A61P 35/00* (2018.01); *C07K 16/18* (2013.01); *C07K 16/28* (2013.01); *C12N 15/09* (2013.01); *C12N 15/1037* (2013.01); *C12Q 1/025* (2013.01); *C12Q 1/68* (2013.01); *G01N 33/15* (2013.01); *G01N 33/6842* (2013.01); *A61K 45/05* (2013.01); *C07K 2317/24* (2013.01); *C07K 2317/33* (2013.01); *C07K 2317/34* (2013.01); *C07K 2317/565* (2013.01); *C07K 2317/76* (2013.01); *C07K 2317/92* (2013.01); *C12N 2310/141* (2013.01); *C12N 2310/16* (2013.01); *C12N 2320/31* (2013.01); *G01N 2570/00* (2013.01)

(58) Field of Classification Search
None
See application file for complete search history.

*Primary Examiner* — Christian C Boesen

(57) ABSTRACT

The present invention is directed to methods for developing novel anti-angiogenic therapies. This invention discovers secretogranin III (Scg3) not only as a novel disease-selective angiogenic factor but also as a target for anti-angiogenic therapy of vascular diseases. Inhibitors against Scg3 can treat diabetic retinopathy, wet age-related macular degeneration, retinopathy of prematurity, retinal vein occlusion, neovascular glaucoma, corneal neovascularization, and cancers.

2 Claims, 11 Drawing Sheets ptosis ligands. Other scientists combined OPD next generation DNA sequencing (NGS) to identify protein-protein binding. However, OPD-NGS has not been used for systematic identification of cellular ligands, disease-specific ligands, receptor-specific ligands or age-related ligands.

The challenges to efficiently identify disease-associated or specific cellular ligands by current OPD technology are: a) low efficiency to thoroughly identify enriched ligands by traditional approaches of manually screening phage clones; b) inability to globally quantify the binding or functional activity of all identified ligands; and c) inability to systematically identify disease-specific or age-related ligands. As a result, all disease-associated ligands are traditionally identified on a case-by-case basis with technical challenges. This has hindered reliable selection of cellular ligands as drug targets for rational design of novel ligand-based therapies.

QUANTITATIVE LIGANDOMICS FOR SYSTEMATIC IDENTIFICATION OF THERAPEUTIC LIGANDS

CROSS-REFERENCES TO RELATED APPLICATIONS

The present application claims the priority of U.S. provisional patent application No. 61/996,616 filed May 12, 2014, which is incorporated herein by reference in its entirety.

STATEMENT REGARDING FEDERALLY SPONSORED RESEARCH OR DEVELOPMENT

This invention was made with government support under GM094449 awarded by the National Institutes of Health/National Institute of General Medical Science. The Government has certain rights in the invention.

BACKGROUND OF THE INVENTION

1. Field of the Invention

The present invention is directed to various methods for systematic identification of disease-specific cellular ligands, age-related ligands and receptor-specific ligands as targets for developing ligand-based therapies.

2. Description of the Related Art

Cellular ligands, such as insulin and vascular endothelial growth factor (VEGF), are valuable targets for ligand-based therapies. Ligands like insulin with beneficial roles can be directly used for disease therapy, whereas ligands with detrimental roles, such as VEGF in angiogenic diseases, can be blocked for therapy. Compared to intracellular proteins, cellular ligands have the advantage for convenient extracellular delivery to access and regulate a broad range of receptor-expressing cells. The barrier to developing new ligand-based therapies is conventional approaches to identify unknown cellular ligands on a case-by-case basis with technical challenges. It is even more daunting to reliably predict which ligands may play a role in disease pathogenesis with therapeutic potentials. Therefore, therapeutic ligands are traditionally identified and characterized in individual cases. Ligandomics to systematically identify cell-wide ligands, disease-specific ligands, age-related ligands or receptor-specific ligands for therapy is currently impossible.

Phage display has been widely used to identify cell-binding antibodies or peptides from antibody libraries or random peptide libraries. Identified antibodies or peptides can be used for cell targeting, drug delivery and disease imaging. However, these antibodies or unnatural peptides are not endogenous ligands to delineate disease mechanisms for rational design of novel ligand-based therapies. Similarly, phage display with conventional cDNA libraries of cellular proteins identifies a high percentage of out-of-frame unnatural short peptides due to uncontrollable reading frames of cellular proteins. Thus, conventional phage display cannot be used to efficiently identify cellular ligands. Despite the combination of conventional phage display with next generation DNA sequencing (NGS), this approach is inefficient to identify endogenous ligands owing to the problem of protein reading frame.

To tackle the problem, open reading frame (ORF) phage display has been developed to identify cellular proteins with specific binding or functional activity, including phagocytosis ligands. Other scientists combined OPD next generation DNA sequencing (NGS) to identify protein-protein binding. However, OPD-NGS has not been used for systematic identification of cellular ligands, disease-specific ligands, receptor-specific ligands or age-related ligands.

SUMMARY OF THE INVENTION

The present invention provides various methods for systematic identification of cell-wide ligands, disease-associated ligands, age-related ligands and receptor-specific ligands that will facilitate new ligand-based therapies for different diseases. The principle of this invention is the combination of phage display, particularly OPD, with NGS for quantitative ligandomics to globally identify ligands with simultaneous binding or functional activity quantification. Quantitative comparison of the entire ligandome profiles will systematically identify disease-associated ligands, age-related ligands or receptor-specific ligands.

Disease-associated or specific ligands are likely involved in disease pathogenesis and therefore are promising candidates to develop novel ligand-based therapies. These ligands with protective or detrimental roles can be expressed or blocked, respectively, for disease therapy.

In a preferred embodiment, cell-based binding selection enriches cell-wide ligands, which are globally identified by NGS with simultaneous binding activity quantification. Quantitative comparison of entire ligandome profiles for diseased versus healthy cells systematically identifies disease-specific ligands. Similar comparison for aged versus young cells identifies entire profiles of age-related ligands.

In similar embodiment, phage selection by PFC enriches cell-wide phagocytosis ligands, which are globally identified by NGS to globally identify phagocytosis ligands with simultaneous quantification of their internalization activities. Quantitative comparison of entire ligandome profiles for diseased versus healthy cells systematically identifies disease-associated phagocytosis ligands. Similar comparison for aged versus young cells identifies entire profiles of age-related phagocytosis ligands.

Cell-based phage selections in this invention can be performed in in vitro or in vivo settings. One of such embodiments is in vivo phage selection to systematically identify disease-associated endothelial ligands. Endothelial ligands are enriched based on their binding activity to endothelium in various organs in vivo and globally identified by NGS with simultaneous binding activity quantification. Quantitative comparison of entire ligandome profiles for diseased versus healthy organs systematically identifies disease-associated endothelial ligands. Similar comparison for aged versus young organs identifies entire profiles of age-related endothelial ligands.

In another embodiment, phage binding selection with receptor-expressing or receptor-deficient/silenced cells enriches cell-wide ligands, which are globally identified by NGS with simultaneous binding activity quantification. Quantitative comparison of entire ligandome profiles for receptor-expressing versus receptor-deficient or silenced cells systematically identifies receptor-specific ligands.

In a similar embodiment, PFC phage selection with receptor-expressing or receptor-deficient/silenced phagocytes enriches cell-wide ligands, which are globally identified by NGS with simultaneous quantification of their internalization activity. Quantitative comparison of entire ligandome profiles for receptor-expressing versus receptor-deficient or silenced phagocytes systematically identifies receptor-specific phagocytosis ligands.

DETAILED DESCRIPTION OF THE INVENTION

Different embodiments include variations in phage selection strategies, cell types and the combination of OPD and NGS for quantitative ligandomics to systematically identify different ligands. These include cell-wide ligands, disease-associated ligands, age-related ligands and receptor-specific ligands to facilitate the development of ligand-based therapies for different diseases.

Figure 1:
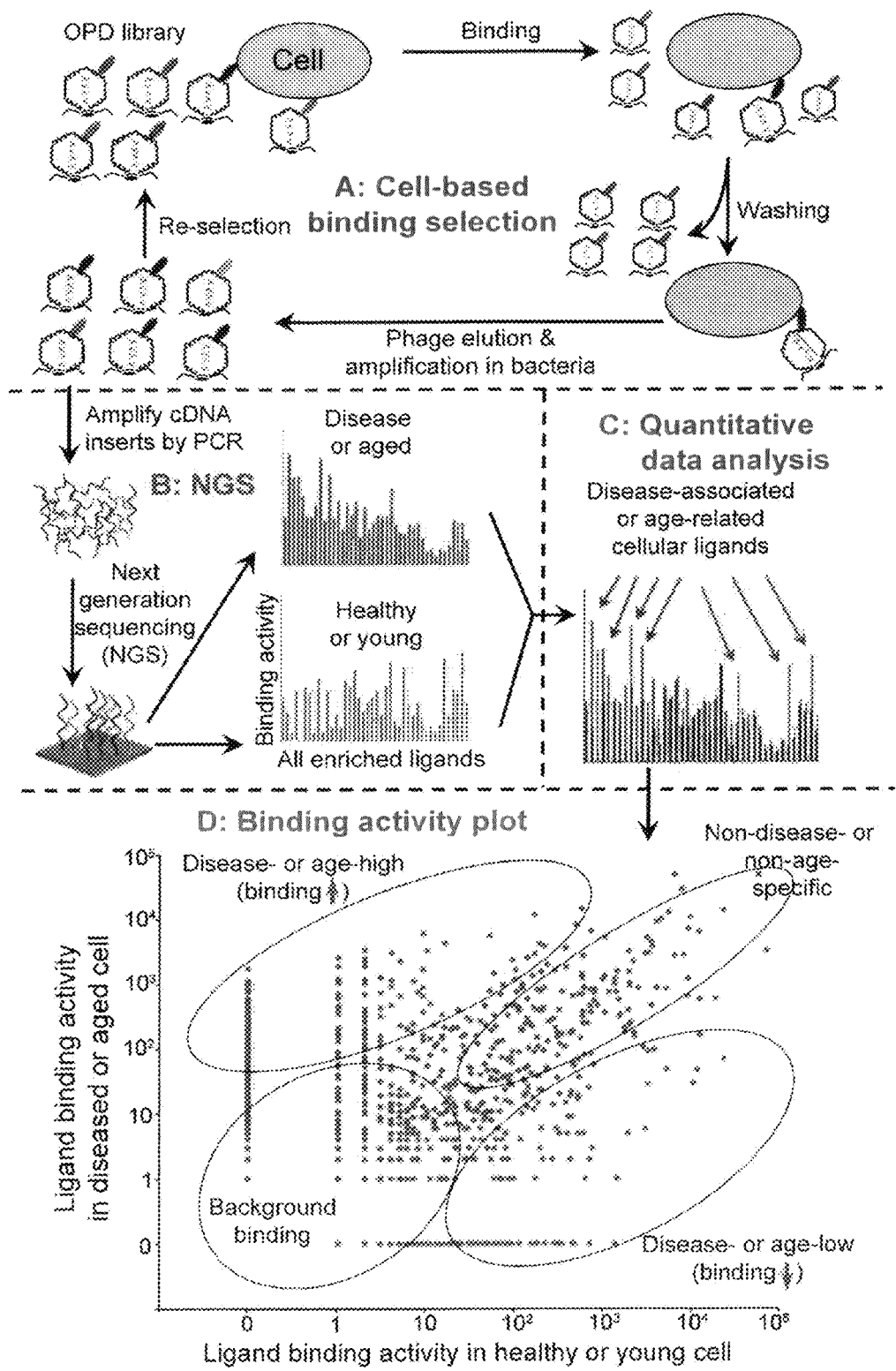
FIG. 1 is a schematic view, showing how ligandomics systematically identifies disease-specific or age-related cellular ligands. (A) Multi-round phage binding selection to enrich cell-binding ligands. (B) NGS to globally identify all enriched ligands. The cDNA inserts of enriched phages are prepared by PCR or restriction digestion and identified by NGS. The copy numbers of the clones identified by NGS are the equivalent of their binding activity. Thus, cell-wide ligands are globally identified by OPD-NGS with simultaneous binding activity quantification like a digital fingerprint map. (C) Quantitative comparison of entire ligandome profiles for diseased versus healthy cells systematically identifies disease-associated ligands. Similarly, quantitative comparison of entire ligandome profiles for aged versus young cells thoroughly identifies age-related ligands. (D) Binding activity plot for diseased vs. healthy cells further divides all identified ligands into four categories: "disease-high" ligands with increased binding to diseased cells; "disease-low" ligands with decreased binding; "non-disease-specific" ligands with minimal binding activity change; and "background binding" with very low binding activity. Similar binding activity plot for aged vs. young cells further divides all identified ligands into "age-high", age-low", "age-independent/non-age-specific" or "background binding". The fingerprint maps and activity plot are for illustration purpose.

In one embodiment (FIG. 1), multiple rounds of cell-based binding selection preferentially enrich phage clones displaying cellular ligands. Cells of interest are incubated with phage libraries. After washing to remove unbound phages, cell-bound phages are eluted by cell lysis, altered pH or protease cleavage (Caberoy et al., 2009, J. Biomol. Screen. 14:653-661; Caberoy et al., 2010, J. Mol. Recognit. 23:74-83). Eluted phages are amplified in bacteria and used as input for the next round of phage selection. The cDNA inserts of enriched phages are extracted either by polymerase chain reaction (PCR) or by restriction digestion, and identified by NGS. Given that NGS is capable of identified hundreds of millions of cDNA inserts per phage sample, all enriched ligands are thoroughly identified by NGS. Because phage clones are enriched based on the binding activity of their displayed ligands, the copy numbers of the cDNA inserts identified by NGS reflect the relative phage enrichment, which in turn reflects the binding activities of the displayed ligands. Therefore, ligandomics globally identifies cell-wide ligands with simultaneous binding activity quantification like a digital fingerprint map. Quantitative comparison of entire ligandome maps or profiles for diseased versus healthy cells systematically identifies disease-related cellular ligands in the absence of receptor information. Binding activity plot for diseased vs. healthy cells further divides all identified ligands into four categories: "disease-high" ligands with increased binding to diseased cells; "disease-low" ligands with decreased binding; "non-disease-specific" ligands with minimal binding activity change; and "background binding" with very low binding activity. Similarly, quantitative comparison of entire ligandome profiles for aged versus young cells identifies age-related cellular ligands. Binding activity plot for aged vs. young cells further divides all identified ligands into "age-high", "age-low", "age-independent/non-age-specific" or "background binding".

Figure 2:
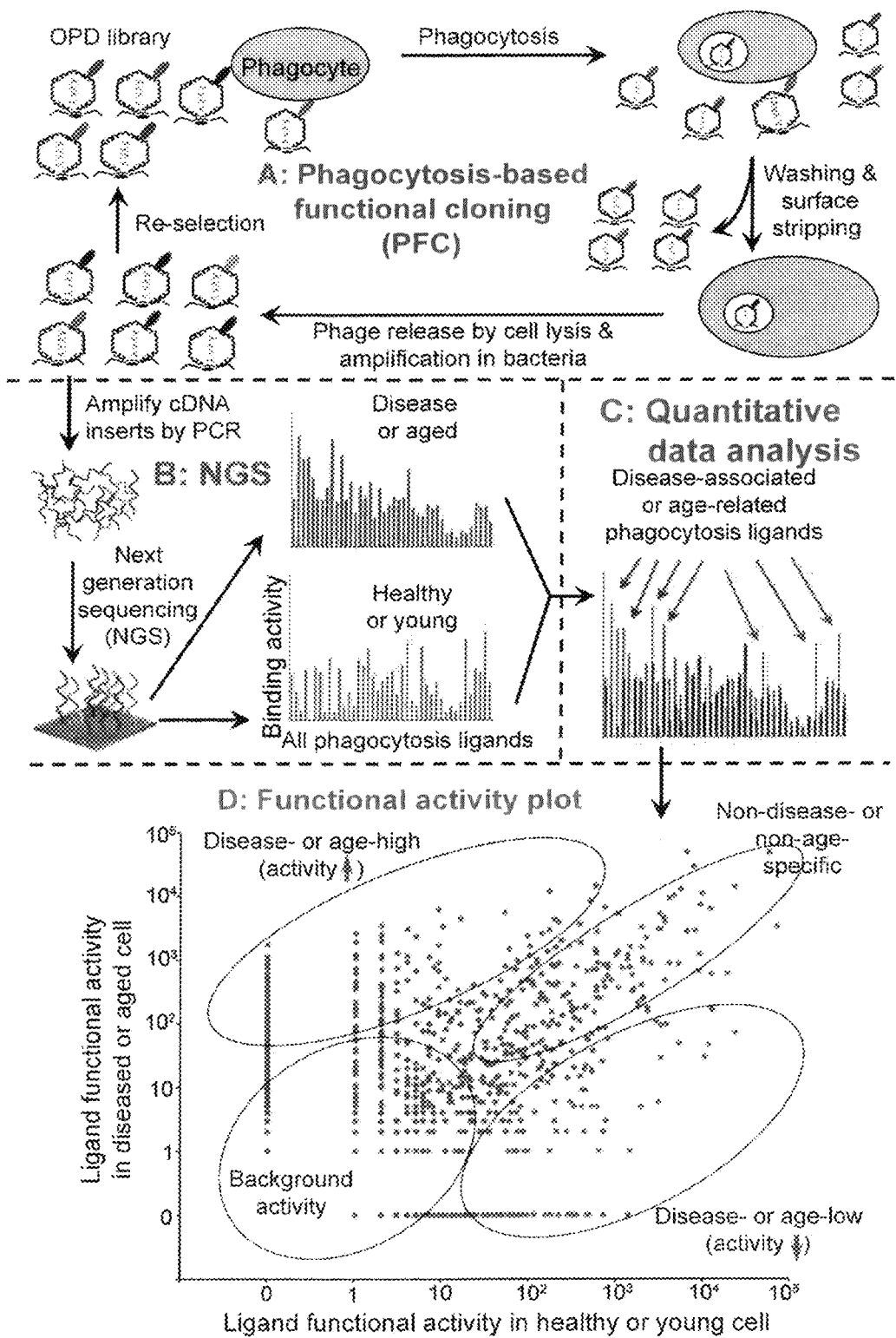
FIG. 2 is a schematic view to illustrate how PFC-based ligandomics systematically identifies disease-associated or age-related phagocytosis ligands. (A) Multi-round phage selection by PFC to enrich cell-wide phagocytosis ligands. (B) NGS to globally identify all enriched ligands. The cDNA inserts of enriched phages are identified by NGS. The copy numbers of the clones identified by NGS are the equivalent of their phagocytosis activity. Thus, cell-wide ligands are globally identified by OPD-NGS with simultaneous functional activity quantification like a digital fingerprint map. (C) Quantitative comparison of entire ligandome profiles for diseased versus healthy phagocytes systematically identifies disease-associated phagocytosis ligands. Similarly, quantitative comparison of the ligandomes for aged versus young phagocytes thoroughly identifies age-related phagocytosis ligands. (D) Activity plot for diseased vs. healthy cells further divides all identified ligands into four categories: "disease-high" ligands with increased phagocytosis activity in diseased cells; "disease-low" ligands with decreased activity; "non-disease-specific" ligands with minimal activity change; and "background activity". Similar functional activity plot for aged vs. young cells further divides all identified ligands into "age-high", age-low", "age-independent/non-age-specific" or "background activity". The fingerprint maps and activity plot are for illustration purpose.

In another embodiment (FIG. 2), multiple rounds of PFC selection preferentially enrich phage clones displaying phagocytosis ligands. The cDNA inserts of enriched phages are identified by NGS. In this case, the copy numbers of the cDNA inserts identified by NGS are the equivalent of the phagocytosis activities of displayed ligands. Thus, ligandomics globally identifies cell-wide phagocytosis ligands with simultaneous functional activity quantification like a digital fingerprint map, Quantitative comparison of entire ligandome maps or profiles for diseased versus healthy phagocytes systematically identifies disease-related phagocytosis ligands in the absence of receptor information. Activity plot for diseased vs. healthy cells further divides all identified ligands into four categories: "disease-high" ligands with increased phagocytosis activity in diseased cells; "disease-low" ligands with decreased activity; "non-disease-specific" ligands with minimal activity change; and "background binding" with very low activity. Similarly, quantitative comparison of entire ligandome profiles for aged versus young phagocytes identifies age-related phagocytosis ligands. Functional activity plot for aged vs. young cells further divides all identified ligands into "age-high", age-low", "age-independent/non-age-specific" or "background binding".

Figure 3:
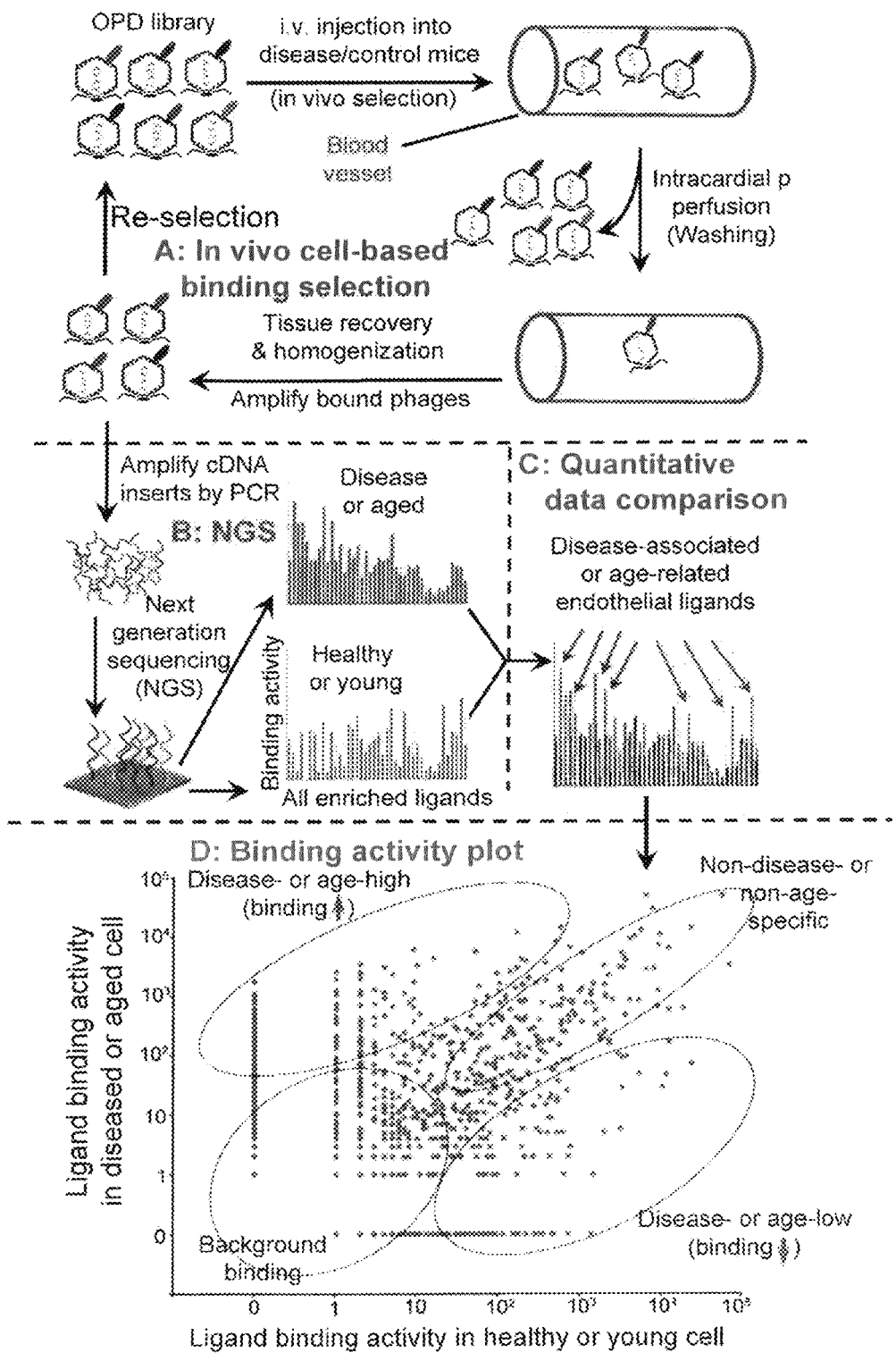
FIG. 3 is a schematic view, showing how ligandomics systematically identifies disease-associated or age-related endothelial ligands in in vivo settings. (A) Multi-round in vivo binding selection to enrich phages displaying endothelial ligands in different organs. (B) NGS to globally identify all enriched ligands. The cDNA inserts of enriched phages are identified by NGS. The copy numbers of the clones identified by NGS are the equivalent of their binding activity. Thus, cell-wide ligands are globally identified by OPD-NGS with simultaneous binding activity quantification like a digital fingerprint map. (C) Quantitative comparison of entire ligandome profiles for diseased versus healthy organs systematically identifies disease-associated endothelial ligands. Similar quantitative comparison for aged versus young organs thoroughly identifies age-related endothelial ligands. (D) Binding activity plot for diseased vs. healthy cells further divides all identified endothelial ligands into four categories: "disease-high" ligands with increased binding to diseased cells; "disease-low" ligands with decreased binding; "non-disease-specific" ligands with minimal binding activity change; and "background binding". Similar binding activity plot for aged vs. young cells further divides all identified endothelial ligands into "age-high", age-low", "age-independent/non-age-specific" or "background binding". The fingerprint maps and activity plot are for illustration purpose.

Ligandomics analysis is broadly applicable to different cells in in vitro or in vivo settings. In FIG. 3, multiple rounds of in vivo binding selection enrich endothelial binding phage clones, which can be globally identified by NGS. Quantitative comparison of entire ligandome profiles for diseased versus healthy organs systematically identifies disease-related endothelial ligands. Binding activity plot for diseased vs. healthy cells further divides all identified endothelial ligands into four categories: "disease-high" ligands with increased binding to diseased cells; "disease-low" ligands with decreased binding; "non-disease-specific" ligands with minimal binding activity change; and "background binding" with very low binding activity. Similarly, quantitative comparison of entire ligandome profiles for aged versus young organs identifies age-related cellular ligands. Binding activity plot for aged vs. young cells further divides all identified endothelial ligands into "age-high", age-low", "age-independent/non-age-specific" or "background binding". Two example experiments are presented below to demonstrate how ligandomics systematically identifies diabetes- or cancer-specific endothelial ligands, delineates their pathological roles and facilitates rational design of novel ligand-based therapies.

Figure 4:
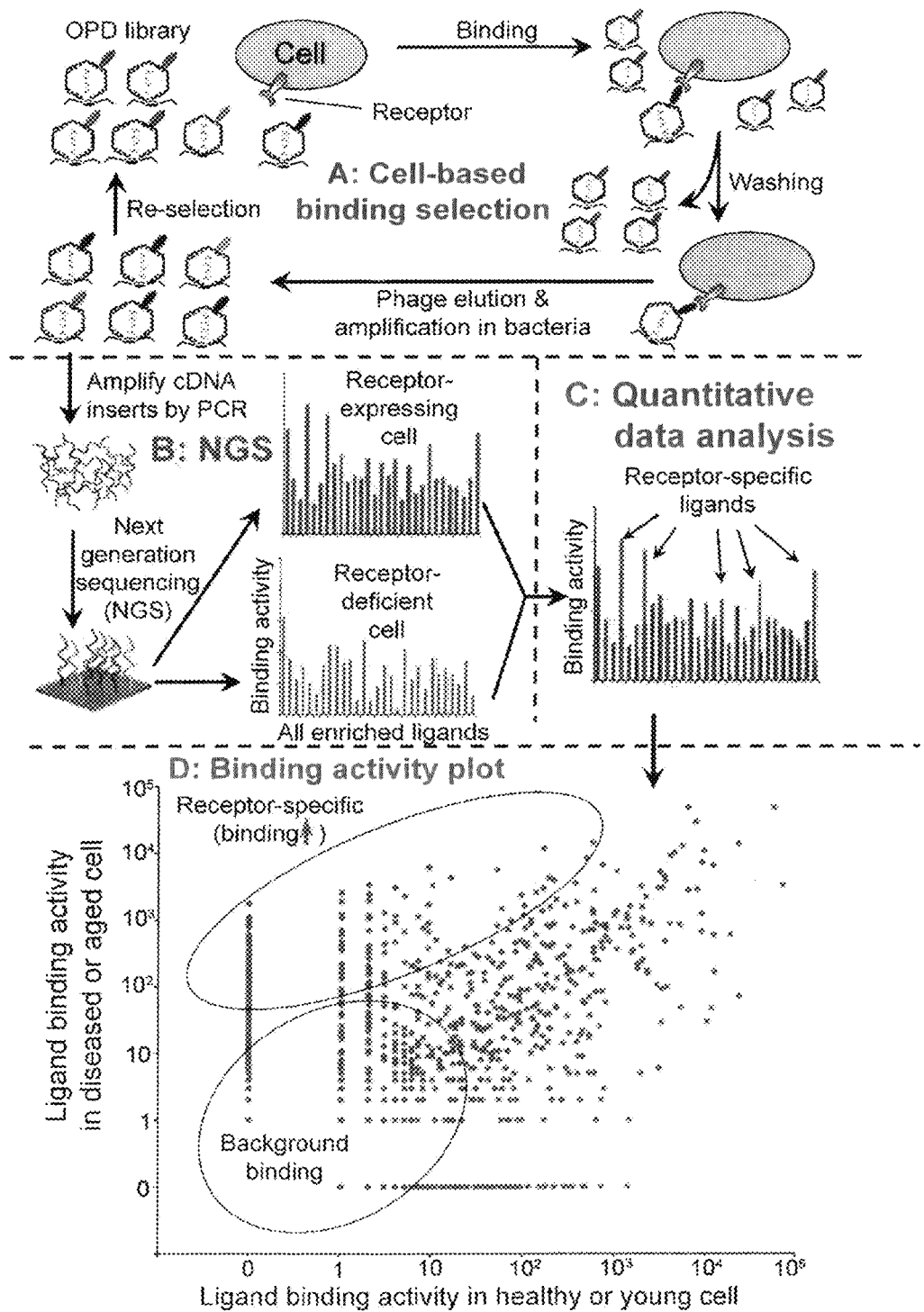
FIG. 4 is a schematic view, showing how to systematically identify receptor-specific ligands with receptor-expressing and receptor-deficient or silenced cells. (A) Multi-round binding selection to enrich cell-wide ligands. (B) NGS to globally identify all enriched ligands with simultaneous binding activity quantification. (C) Quantitative comparison of entire ligandome profiles for receptor-expressing versus receptor-deficient or silenced cells systematically identifies receptor-specific ligands. (D) Binding activity plot for receptor-expressing vs. receptor-deficient or silenced cells further identifies "receptor-specific" ligands with increased binding to receptor-expressing cells. The fingerprint maps and activity plot are for illustration purpose.

In yet another embodiment, ligandomics analysis by OPD-NGS globally maps receptor-specific ligands (FIG. 4). Multiple rounds of cell-based binding selection enriches cell-wide ligands by ligandomics. All enriched ligands are identified by NGS with simultaneous binding activity quantification. Quantitative comparison of their entire ligandome profiles for receptor-expressing versus receptor-deficient or silenced cells systematically identifies receptor-specific ligands.

Figure 5:
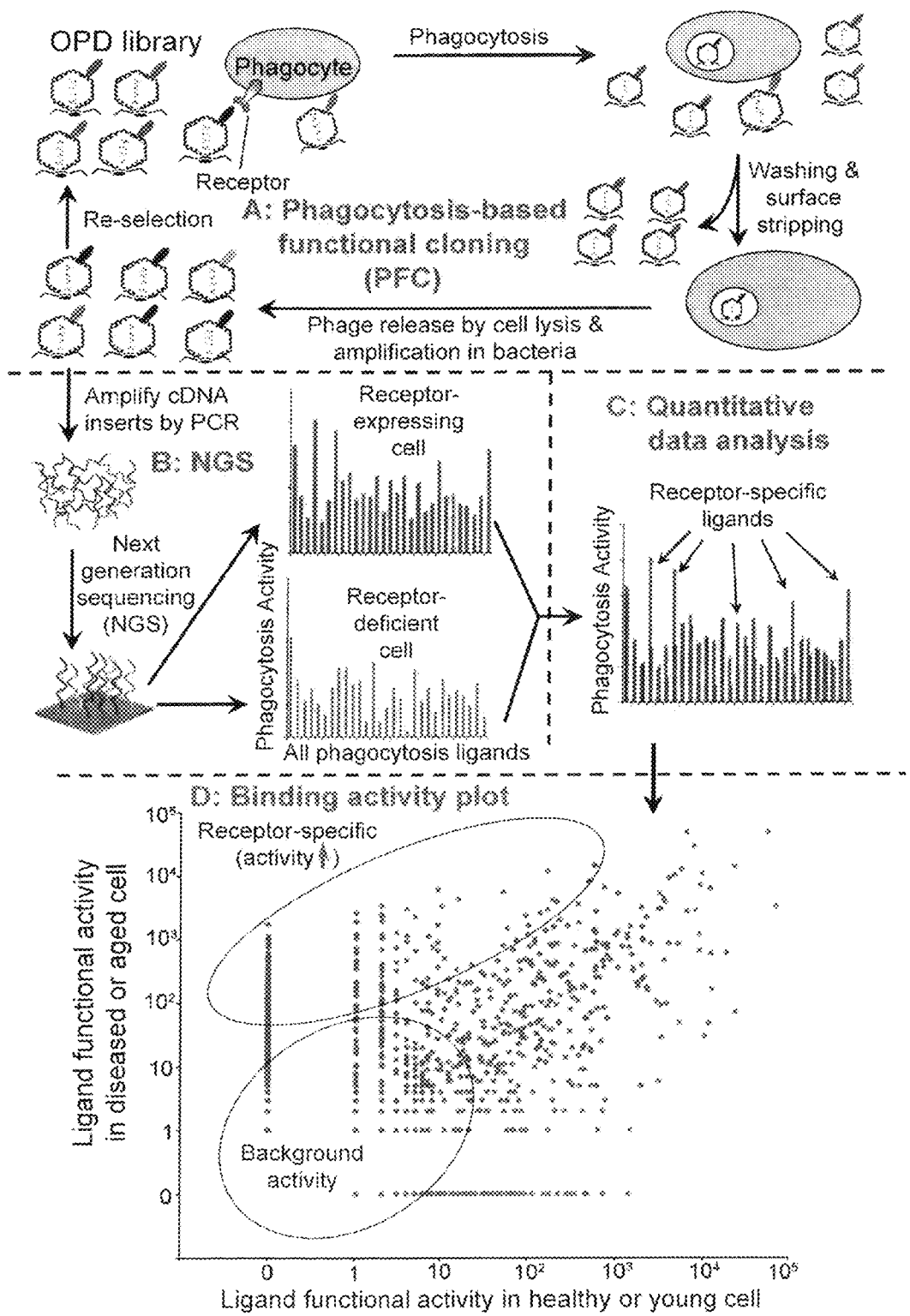
FIG. 5 is a schematic view, showing how to systematically identify receptor-specific phagocytosis ligands with receptor-expressing and receptor-deficient or silenced phagocytes. (A) Multi-round phage selection by PFC to enrich cell-wide phagocytosis ligands. (B) NGS to globally identify all enriched ligands with simultaneous phagocytosis activity quantification. (C) Quantitative comparison of entire ligandome profiles for receptor-expressing versus receptor-deficient or silenced phagocytes systematically identifies receptor-specific phagocytosis ligands. (D) Activity plot for receptor-expressing vs. receptor-deficient or silenced cells further identifies "receptor-specific" ligands with increased phagocytosis activity in receptor-expressing cells. The fingerprint maps and activity plot are for illustration purpose.

In a similar embodiment, ligandomics by OPD-NGS globally identifies receptor-specific phagocytosis ligands (FIG. 5). Multiple rounds of PFC-based selection enriches cell-wide phagocytosis ligands. All enriched phagocytosis ligands are identified by NGS with simultaneous functional activity quantification. Quantitative comparison of their entire ligandome profiles for receptor-expressing versus receptor-deficient or silenced cells systematically identifies receptor-specific phagocytosis ligands.

Disease-high ligands with their cognate receptors upregulated on cell surface are more likely to have increased pathogenic or protective roles in disease pathogenesis than disease-low ligands or non-disease-specific ligands. Similarly, age-high ligands are more likely to have increased pathogenic or protective roles in aging process than age-low ligands or age-independent ligands. Disease-high ligands with protective roles can be directly used for new therapies. Disease-high ligands with detrimental roles can be blocked to develop novel therapies. In contrast, it is more difficult to exploit the therapeutic potential of disease-low ligands because of the downregulation of their receptors on diseased cells.

Quantitative ligandomics can be applied to any healthy or diseased cells. For example, ligandomics analysis for cancer cells versus healthy cells will identify cancer-specific binding ligands. Cancer-high ligands with increased binding to cancer cells can be further analyzed for their role in cancer regulations, such as apoptosis, proliferation, survival, differentiation, adhesion, etc. Ligands with protective roles, such as inducing cancer cell apoptosis, can be directly used for cancer therapy. Ligands with detrimental role, such as inducing cancer proliferation, can be blocked for cancer therapy. Ligandomics analysis for stem cells versus differentiated cells will identify stem cells-specific ligands.

Any type of isolated cells, including various cell lines or primary cells, can be used for ligandomics analysis. Cells in live hosts, such as endothelial cells of live mice in Example 1, can be used for ligandomics analysis. Quantitative ligandomics may also be applied to isolated tissues or organs with cell binding or phagocytosis selection.

ORF phage display cDNA libraries (U.S. Pat. No. 8,754,013) are preferred for various embodiments of quantitative ligandomics. Conventional phage display cDNA libraries of cellular proteins include both ORF clones and non-ORF clones are also suitable to ligandomics analysis by OPD-NGS and DFC-NGS. However, because of high percentage of out-of-frame phage clones, conventional phage display has low efficiency to identify endogenous cellular ligands.

Phage display has been developed with different vectors, including various filamentous phages (M13, fl and fd), T7 phage, lambda phage and T4 phage. The ORF cDNA libraries of all these phage vectors can be constructed and combined with NGS for ligandomics analysis to systematically map cell-wide ligands, disease-related ligands, age-related ligands and receptor-specific ligands.

EXAMPLES

The following examples are intended to illustrate certain embodiments of the methods and demonstrate how the discovery of disease-specific ligands by the methods led to rationale design of ligand-based therapies. These examples are not intended to limit the scope of the invention.

Example 1

Systematic Identification of Diabetes-Specific Endothelial Ligands

Diabetes affects ~25.8 million people in the U.S. or 8.3% of the population. Diabetic vascular complications (DVCs), such as heart attacks, atherosclerosis, diabetic retinopathy (DR), diabetic nephropathy, diabetic neuropathy and diabetic foot, are the major causes of morbidity and mortality of diabetes. DR is a leading cause of vision loss in working adults, affecting ~7.7 million people in the U.S. Nearly all individuals with type 1 diabetes and more than 60% of individuals with type 2 diabetes have some degree of DR after 20 years of diabetes onset. About one third of the diabetic population have signs of DR, and approximately one tenth have vision-threatening retinopathy, such as proliferative DR (PDR) and diabetic macular edema (DME).

DR is characterized by increased vascular permeability, endothelial apoptosis, acellular capillaries, leukocyte adhesion, late-onset angiogenesis, retinal bleeding and vision impairment. In 2012, Lucentis (ranibizumab) was approved as the first drug to treat DME. Various clinical trials indicated that the therapeutic efficacy of Lucentis for DME is ~21-37% (average ~28%) (Virgili et al., 2014, Cochrane Database Syst. Rev. 10:CD007419, PMID, 25342124). The approval of Lucentis generated a surge in developing different anti-VEGF drugs for DME, such as Eylea (aflibercept from Regeneron Pharmaceuticals, Inc., approved by the FDA in 2014) and conbercept (in clinical trial, Konghong Parmaceutical), both of which are soluble VEGF receptors. Other approved anti-VEGF drugs for different diseases, including Avastin (bevacizumab) and Macugen (pegaptanib, an RNA aptamer), were also reported for clinical trials with DME patients. This wave of research highlights anti-angiogenesis therapy of DME as a major breakthrough. However, the challenge to further improve the therapeutic efficacy is how to delineate other pathogenic angiogenic ligands and develop additional therapies for anti-VEGF-resistant DME.

FIG. 3 illustrates an embodiment of this invention to identify DR-specific angiogenic ligands and facilitate novel anti-angiogenesis therapies.

In Vivo Binding Selection

Mice (C57BL/6, 6 weeks old, female) were induced for type 1 diabetes with streptozotocin (STZ) (starving for 4 h, followed by 50 µg STZ/g body weight, for 5 consecutive days) or mock citrate buffer to destroy pancreatic islet cells, as described (Chen et al., 2013, Diabetes 62:261-271). Mice were monitored for blood glucose by biweekly and considered diabetic when the blood glucose was >350 mg/dL, usually starting at 2-4 weeks post STZ treatment. Mice at 4 months post STZ treatment (4-month-diabetic mice) were used for the study.

Two OPD cDNA libraries of mouse embryos and eyes have been described in the literature (Caberoy et al., 2009, Biochem. Biophys. Res. Commun. 386:197-201; Caberoy et al., 2010, J Mol. Recognit. 23:74-83). Both libraries were amplified, purified by CsCl centrifugation, dialyzed against PBS and titrated by plaque assay according to T7Select System Manual from Millipore. Both libraries were pooled together in equal titer and intravenously injected into 4-month-diabetic and control mice (~1×10$^{12}$ plaque forming units (pfu)/mouse) for in vivo binding selection (FIG. 3A), as described (Arap et al., 1998, Science 279:377-80). After 20-min circulation, unbound phages were removed by intracardial perfusion. The retinas were isolated with endothelium-bound phages, which were released by tissue homogenization in PBS with 1% Triton X-100, quantified by phage plaque assay (Caberoy et al., 2010, J. Mol. Recognit. 23:74-83), amplified in bacteria and used as input for the next round of the selection. After 3 rounds of in vivo selection, the cDNA inserts of enriched phage clones were amplified by PCR and identified by NGS.

To assess the reliability of binding activity quantification, two clonal phages displaying human VEGF (VEGF-Phage) and green fluorescent protein (GFP-Phage) were constructed. Both clonal phages were spiked into the mouse OPD library at 1:1,000 before in vivo binding selection. After 3 rounds of selection, VEGF-Phage and GFP-Phage with non-mouse codons were simultaneously identified by NGS along with enriched mouse library clones.

Ligandomics Analysis.

The results showed that a total of 489,126 and 473,965 valid sequence reads were identified by NGS for diabetic and control retina and matched to 1,548 and 844 ligands in NCBI CCDS database, respectively (Table 1).

Figure 6:
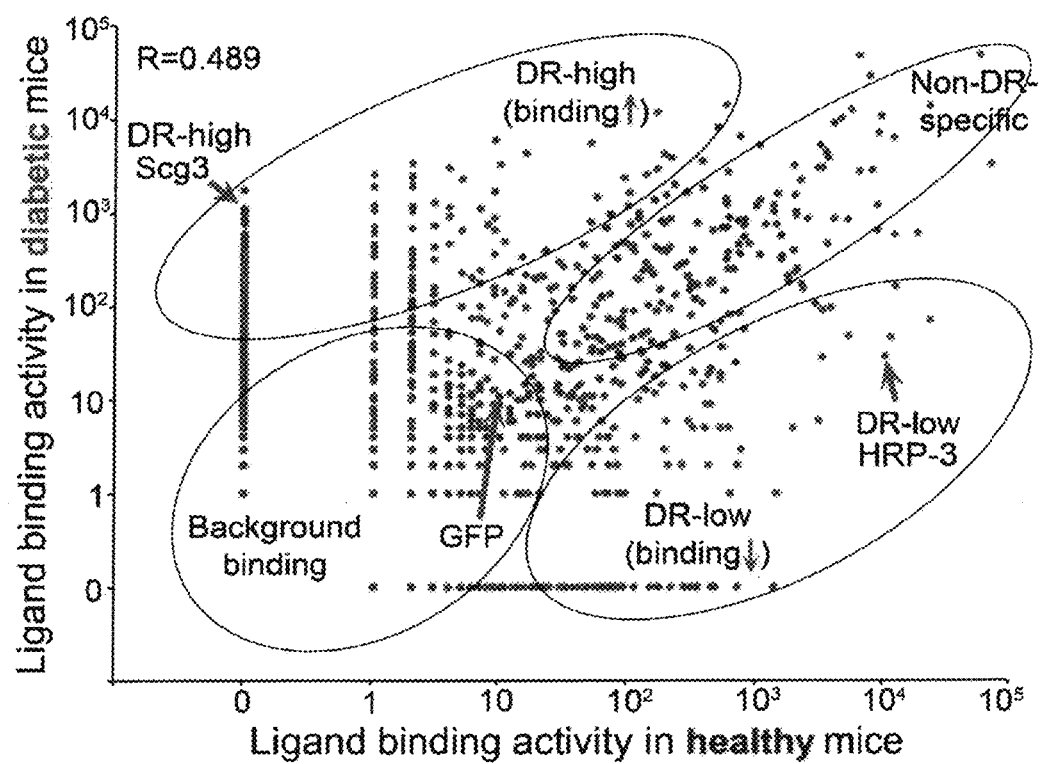
FIG. 6 is an actual graph of binding activity plot, showing systematic profiling of disease-specific endothelial ligands in diabetic mice. Ligandomics was performed in 4-month-diabetic and control mice, as described in FIG. 3. All identified ligands with binding activity to retinal endothelium were quantitatively compared by binding activity plot to identify diabetes-specific ligands. Secretogranin III (Scg3) and hepatoma-derived growth factor related protein 3 (HRP-3) were identified as diabetes-high and diabetes-low ligands, respectively. Pearson correlation coefficient R=0.489.
Figure 7:
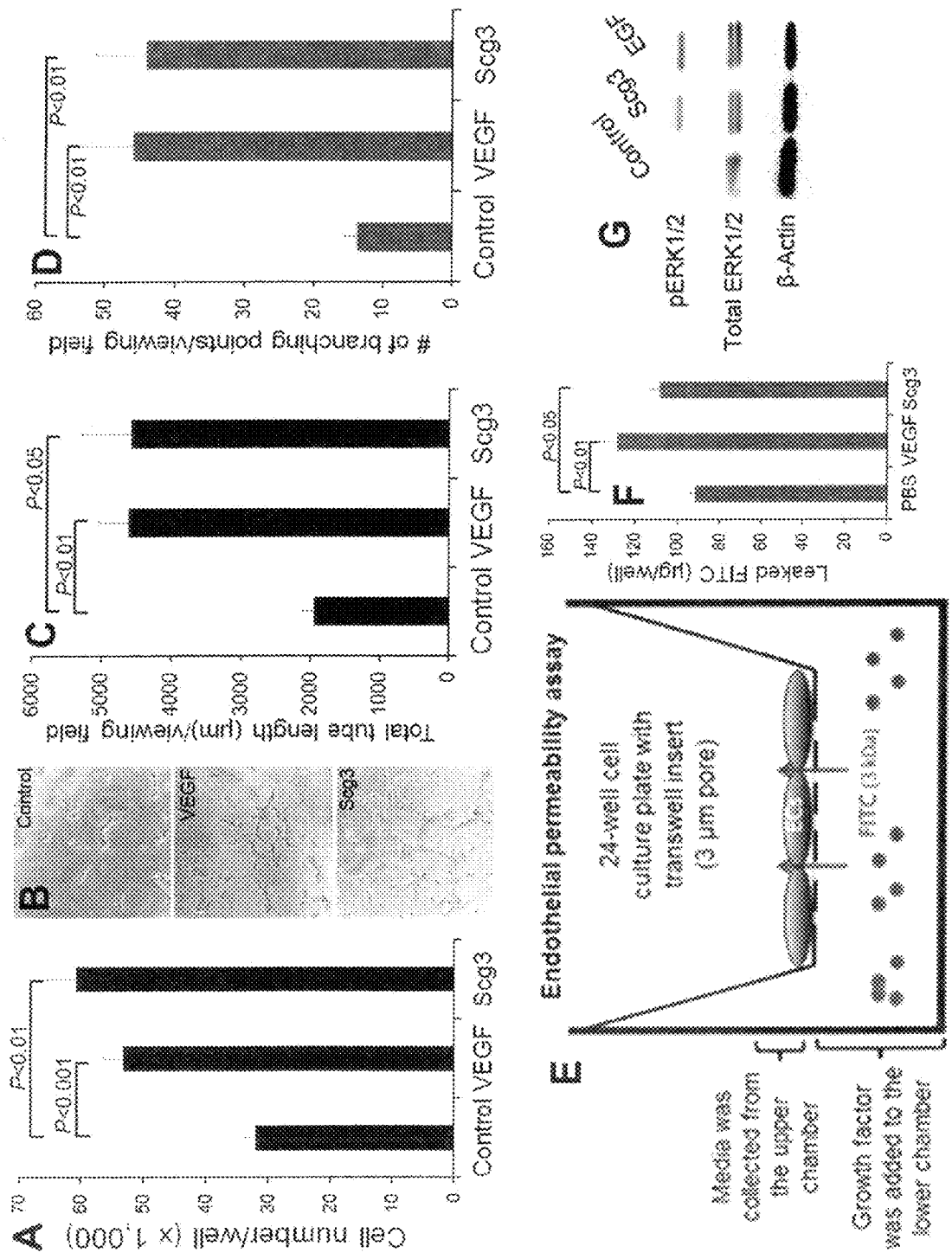
FIG. 7 is characterizations of Scg3 as an angiogenic factor by different in vitro functional assays. (A) Cell proliferation assay with human umbilical vein endothelial cells (HU- VECs). Cells were plated in 48-well plates and incubated with VEGF165 (50 ng/ml), Scg3 (1 µg/ml) or PBS control for 48 h. Total cell number in each well were counted (n=4). (B-D) are tube formation assay. (B) Images of tube formation. HUVECs were incubated with VEGF (50 ng/ml), Scg3 (300 ng/ml) or PBS for 3 h. (C) Quantification of total tube length in FIG. 7B (n=4). (D) Quantification of branching points in FIG. 7B (n=4). (E,F) Endothelial permeability assay. (E) Cartoon illustration of the permeability assay. (F) Quantification of leaked fluorescein (FITC)-dextran (3 kDa) at 24 h. Scg3, 200 ng/ml; VEGF, 100 ng/ml; n=3. (G) Western blot analysis of Scg3-induced ERK activation. EGF (epidermal growth factor) is a positive control. Scg3, 1 µg/ml; EGF, 100 ng/ml. All data are mean±s.e.m., Student's t-test.

The copy numbers of the cDNA inserts identified by NGS are the equivalent of relative binding activity for the cognate displayed ligands. The depletion of GFP-Phage and relative enrichment of VEGF-Phage by three rounds of in vivo selection in Table 1 confirmed that this method of quantification reflected their differential binding activities in vivo. Additionally, the results support the use of GFP-Phage as a baseline of non-specific binding to distinguish positive ligands (FIG. 6).

TABLE 1

DR-specific endothelial ligands identified by quantitative ligandomics

| CCDS_ID | Protein | Binding activity DR | Control | Activity ratio |
|---|---|---|---|---|
| DR-high ligands with increased binding to diabetic ECs |  |  |  |  |
| CCDS23347.1 | Scg3* | 1,731 | 0 | 1,732 |
| CCDS18810.1 | C1qb* | 837 | 0 | 838 |
| CCDS28285.1 | APP* | 206 | 1 | 104 |
| DR-low ligands with decreased binding to diabetic ECs |  |  |  |  |
| CCDS40011.1 | HRP-3* | 48 | 11,140 | 0.0044 |
| Internal negative control |  |  |  |  |
|  | VEGF-Phage | 408 | 2,420 | 0.1689 |
|  | GFP-Phage | 10 | 10 | 1.0 |
|  | Total identified sequences | 489,126 | 473,965 |  |
|  | Total identified ligands | 1,548 | 844 |  |
|  | Diabetes-related ligands* | 277↑ | 89↓ |  |

*P ≤ 0.001.
DR vs. control,
$\chi^2$ test.
All binding activities are normalized for quantitative data comparison.
If normalized activity is < 0.5, it is listed as zero.
Activity ratio = (DR + 1)/(Control + 1).

The global pattern of binding activity changes in DR was analyzed by a binding activity plot (FIG. 6). The results indicated that endothelial binding activities of the entire ligandome were markedly altered in 4-month-diabetic mice with Pearson correlation coefficient (R) of 0.489. A large number of DR-high and DR-low ligands were identified, suggesting that their cognate receptors on the endothelial cells (ECs) were up- or down-regulated. Quantitative comparison of the entire ligandome profiles for diabetic vs. control retina by $\chi^2$ test identified 277 DR-high and 89 DR-low ligands (Table 1).

Not all identified ligands are angiogenic factors. Some ligands may regulate apoptosis and proinflammatory response. For example, two known diabetes-associated endothelial ligands identified were amyloid precursor protein (APP) and C1qb. Amyloid β (Aβ) derived from APP is a known endothelial ligand that binds to RAGE (receptor for advanced glycation end products), which is upregulated on diabetic ECs (Manigrasso et al., 2014, Trends Endocrinol. Metab. 25:15-22). C1qb is the β subunit of C1q complement factor that interacts with two endothelial receptors, cC1qR and gC1qR/p33, to produce proinflammatory cytokines (Kishore and Reid, 2000, Immunopharmacology 49:159-170). C1q is present in significant quantities at the site of atherosclerotic lesions (Peerschke et al., 2004, Mol. Immunol. 41:759-766), which are hallmarks for diabetic vascular complications. Thus, both C1qb and APP support the validity of ligandomics to identify diabetes-associated endothelial ligands.

Scg3 is Identified as a Novel Angiogenic Factor

Secretogranin III (Scg3) (GenBank accession # NM_013243 and MN_001165257 for human Scg3; NM_009130 and NM_00164790 for mouse Scg3) was identified by quantitative ligandomics in diabetic mice (Table 1). Scg3 has never been reported as an endothelial ligand before. Based on the literature, Scg3 is predicted as a putative angiogenic factor as follows. Scg3 belongs to the family of multifunctional secretogranins. Its family member, secretogranin II (Scg2), is a prohormone of secretoneurin with angiogenic activity (Kirchmair et al., 2004, Circulation 110:1121-1127). The functional role of Scg3 is poorly defined. A previous study showed that Scg3 was secreted from dysfunctional β-cells and therefore may be upregulated in type 1 diabetes (Dowling et al., 2008, Electrophoresis 29:4141-4149). Proteomics data indicated that Scg3 is released from activated platelets and is upregulated in atherosclerosis (Coppinger et al., 2004, *Blood* 103:2096-2104), which is one of the vascular complications in diabetes. Increased expression of Scg3 was reported in hepatocellular carcinoma (Wang et al., 2014, *Cancer Lett.* 352:169-178).

Scg3 was independently characterized as an angiogenic factor by various in vitro angiogenesis assays, including endothelial proliferation assay, tube formation assay and permeability assay (FIG. 7A-7F). For cell proliferation assay, human umbilical vein endothelial cells (HUVECs) were incubated with VEGF165 (50 ng/ml), Scg3 (1 μg/ml) or PBS control in 48-well plates for 48 h. Cell number per well was quantified. Similar results were obtained with human retinal microvascular endothelial cells (HRMVECs) (see FIG. 9A). Tube formation assay was performed, as described (Su et al., 2006, *FASEB J.* 20:1443-1451). Briefly, 96-well plates were pre-coated with growth factor-reduced Matrigel (Corning). HUVECs were plated in Matrigel-coated wells and incubated with VEGF (50 ng/ml), Scg3 (300 ng/ml) or PBS for 3 h. Cell images were photographed and quantified for total tube length or branching points per viewing field. Endothelial permeability assay was performed as described (Martins-Green et al., 2008, *Methods Enzymol.* 443:137-153). Briefly, HUVECs were cultured on transwell inserts until confluence. Scg3 (200 ng/ml), VEGF (100 ng/ml) or PBS was added to the top chamber, and FITC-dextran (3 kDa, Sigma) was added to the bottom chamber. After 24 h, the leaked FITC in the top chamber was quantified. Additionally, signaling studies revealed that ERK1/2 was activated by Scg3 in HUVECs (FIG. 7G). The method of ERK activation assay was described in a previous study (Xiao et al., 2013, *Gut* 62:440-451). The results of all these functional assays suggest that Scg3 is an angiogenic factor.

Scg3 as a Diabetes-High Angiogenic Factor

Scg3 and hepatoma-derived growth factor related protein 3 (Hdgfrp3, or HRP-3) were identified by quantitative ligandomics as a DR-high and DR-low endothelial ligands, respectively (FIG. 6). In vivo corneal pocket angiogenesis assays were performed as described (Coxon et al., 2002, *Arthritis Rheum.* 46:2604-2612). Briefly, sterilized Whatman filter paper (Grade 3) (GE Healthcare Bio-Sciences, Piscataway, N.J.) was cut into pieces (0.125 mm$^2$/piece). The papers were soaked in the solution of HRP-3, VEGF or PBS for 2 h at 4° C., and implanted into corneal pockets in anesthetized C57BL/6 mice (8-10 weeks old; 1 paper/cornea; 2 pockets/mouse). After 6 days, angiogenesis in each eye was evaluated using a slit-lamp microscope and photographed. The number of new sprouting vessels into the cornea and their branching points were quantified. In addition, corneal angiogenesis was semiquantitatively scored to analyze the number, density, length of visible corneal blood vessels, as described (Yuan and Wilhelmus, 2009, *Mol. Vis.* 15:1988-1896). The mice were then euthanized by $CO_2$, and immediately perfused intracardially with lipophilic fluorescent DiI dye (Li et al., 2008, *Nat. Protoc.* 3:1703-1708).

Figure 8:
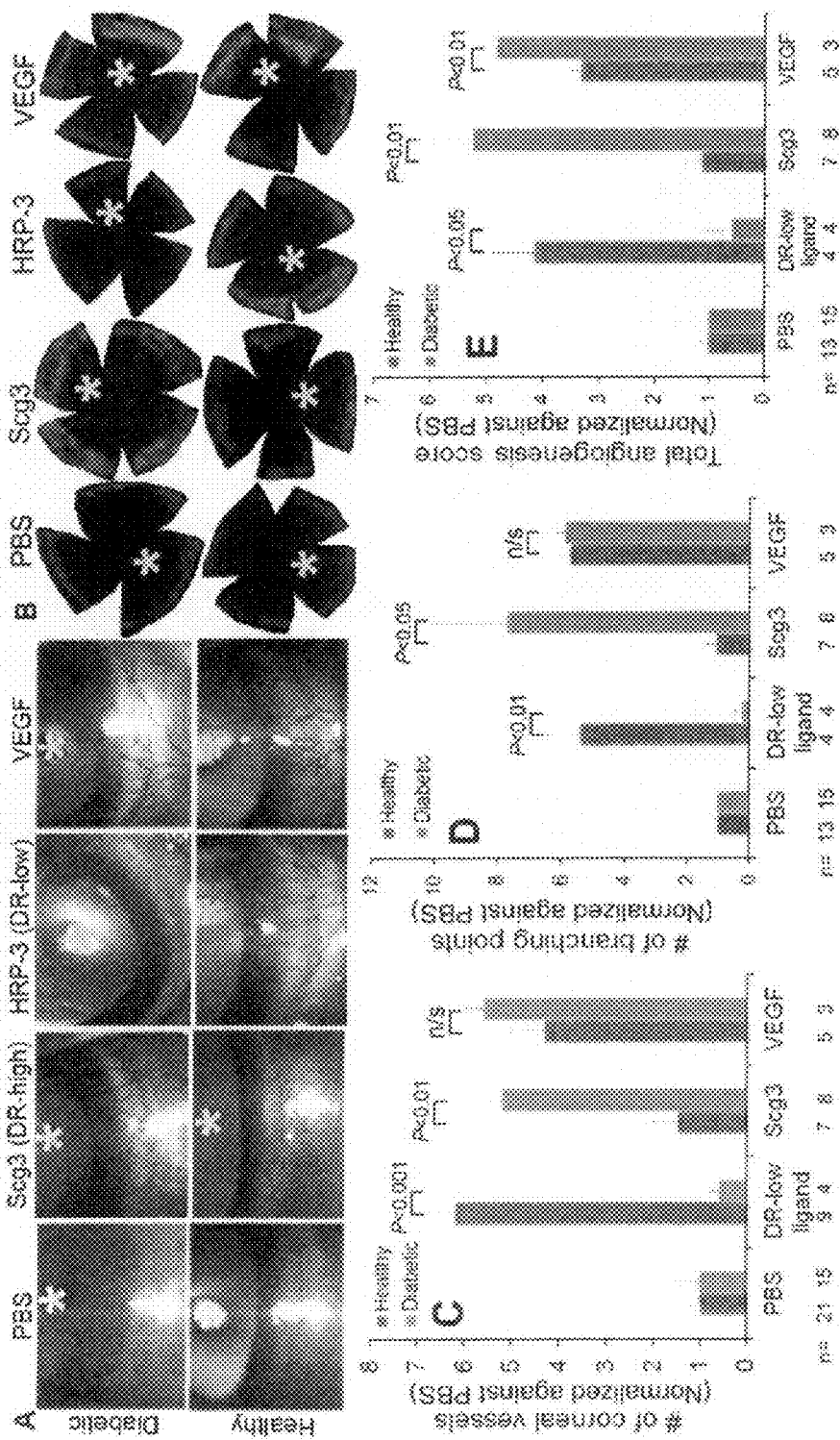
FIG. 8 shows that Scg3 and HRP-3 are diabetes-high and diabetes-low angiogenic ligands, respectively. Corneal pocket angiogenesis assay was performed in 4-month-diabetic and control mice. Small pieces of filter papers pre-soaked in Scg3 (250 ng/µl), HRP-3 (1 µg/µl), VEGF (100 ng/µl) or PBS were implanted in corneal pockets to induce vascular sprouting into the cornea for 6 days. (A) Representative images of corneal angiogenesis. (B) DiI fluorescence dye labeling of corneal blood vessels. (C-E) Quantification of corneal angiogenesis 6 days post implantation of angiogenic factor. (C) The number of corneal vessel number, (D) the number of branching point. (E) Total angiogenesis score. * indicates the position of implanted angiogenic factor. Sample sizes are indicated at the bottom.±s.e.m, one-way ANOVA test.

The results showed that that Scg3 is more angiogenically active in diabetic mice than in control mice (FIG. 8), supporting that Scg3 is a DR-high angiogenic ligand. In contrast, HRP-3 showed an opposite pattern of preferential activity to stimulate angiogenesis in control mice. VEGF is equally activity in 4-month-diabetic and control mice. The distinct activity patterns of Scg3, HRP-3 and VEGF in diabetic and control mice strongly support the validity of quantitative ligandomics as a discovery science for systematic identification of disease-specific ligands. Furthermore, these data also imply that Scg3 and VEGF regulate angiogenesis through different receptors, providing an opportunity for alternative or combination anti-angiogenic therapy for DR. To determine if the selection of DR-high Scg3 is due to serendipity, HRP-3 was included as a DR-low control angiogenic factor. Corneal pocket assay showed that HRP-3 had an opposite pattern of angiogenic activity to Scg3. It is angiogenically active only in healthy mice but not diabetic mice. The distinct patterns of angiogenic activity for DR-high Scg3 and the DR-low HRP-3 in diabetic and control mice strongly validate the innovative discovery science of quantitative ligandomics for systematic identification of disease-specific ligands.

Rational Design of Ligand-Based Therapies for Diabetic Retinopathy

Figure 9:
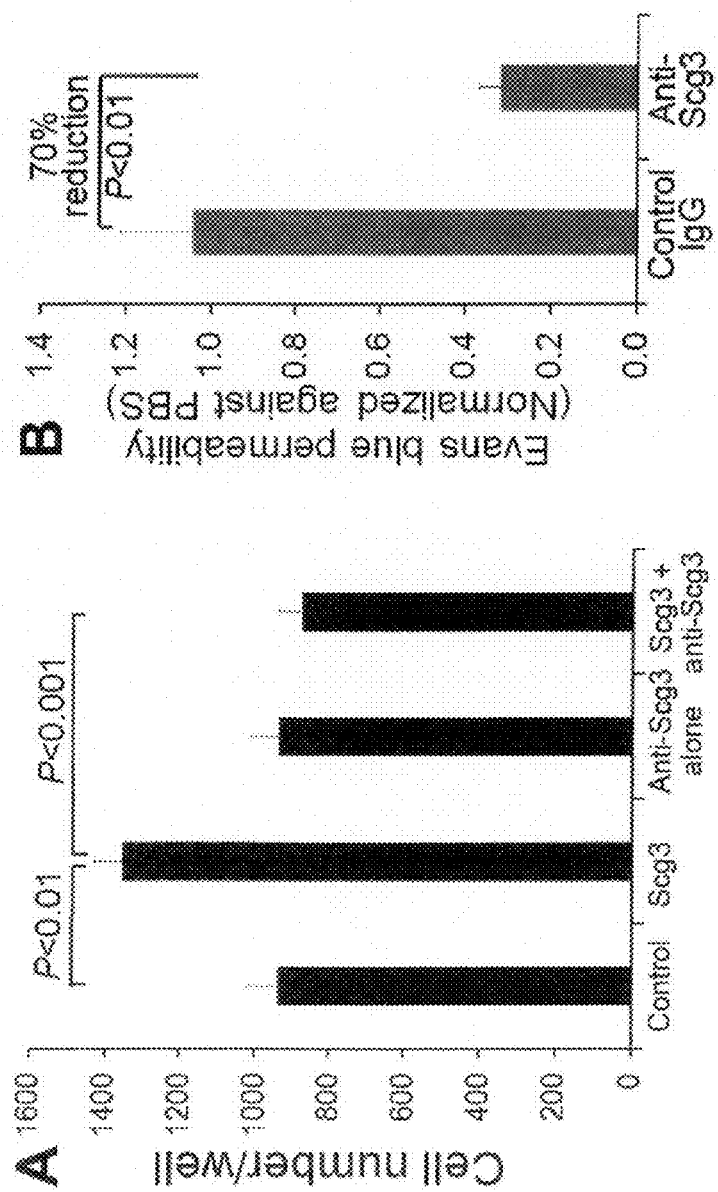
FIG. 9 is graphs showing that anti-Scg3 therapy alleviated retinal vascular leakage in 4-month-diabetic mice. (A) Affinity-purified anti-Scg3 polyclonal antibody neutralizes Scg3-induced proliferation of human retinal microvascular endothelial cells (HRMVECs). Cells in 96-well plates were cultured with Scg3 (1 µg/ml), anti-Scg3 Ab (2 µg/ml), Scg3 plus the antibody, or PBS control (n=8). (B) Anti-Scg3 therapy alleviates diabetic retinal vascular leakage. Affinity-purified anti-Scg3 polyclonal antibody or control IgG (0.36 µg/1 µl/eye) was intravitreally injected into one eye of 4-month-diabetic mice with PBS for the contralateral eye. Evans blue was intravenously injected to quantify retinal vascular leakage at 4 h post therapy. Data are normalized against PBS and expressed as percentage of reduction in leakage (n=5).±s.e.m., one-way ANOVA test.

VEGF inhibitors, such as Lucentis and Eylea, have been approved for clinical therapy of DME. Scg3 was also investigated for its potential for anti-angiogenesis therapy of diabetic retinal vascular leakage as follows. Affinity-purified polyclonal anti-Scg3 antibody was verified for its capacity to block Scg3-induced proliferation of HRMVECs (FIG. 9A). Evans blue assay was used to investigate the effectiveness of anti-Scg3 therapy for preventing retinal vascular leakage, as previously described (Xu et al., 2001, *Invest. Ophthalmol. Vis. Sci.* 42:789-794). Briefly, affinity-purified anti-Scg3 polyclonal antibody or control IgG (0.36 μg/1 μl/eye) was intravitreally injected into one eye of 4-month-diabetic mice with PBS for the contralateral eye. PBS control is necessary because STZ induces diabetes in different mice with variable severity in DR. One and half an hour later, Evans blue was intravenously injected and allowed to be circulated for additional 2.5 h. After intracardial perfusion, retinas were isolated and incubated with formamide overnight to extract leaked Evans blue. After ultracentrifugation, extracted Evans blue was quantified at $OD_{620}$ and normalized against retinal weight as well as Evans blue in the plasma. The results for anti-Scg3 antibody and control IgG were further normalized against contralateral eye treated with PBS. The results showed that anti-Scg3 antibody alleviates retinal vascular leakage in diabetic mice (FIG. 9B). These results suggest Scg3 is a promising target to develop anti-angiogenic therapy for DR.

Anti-Scg3 Therapy for Vascular Age-Related Macular Degeneration

Age-related macular degeneration (AMD) is a leading cause of vision loss in the U.S. An estimated 2.07 million people had AMD in 2010. This number is expected to be more than doubled to 5.44 million in 2050 in the U.S. Vascualr or wet AMD with choroidal neovascularization (CNV) affects 10-15% of individuals with the disease but accounts for ~90% of all cases with severe vision loss from the disease. Angiogenic factors play an important role in the pathogenesis of wet AMD.

Anti-VEGF drugs, Lucentis and Eylea, have been approved for the therapy of both wet AMD and DME. Because of the therapeutic activity of anti-Scg3 antibody for diabetic retinal vascular leakage (FIG. 9B), the anti-Scg3 antibody was further investigated for the therapy of wet AMD as follows.

Figure 10:
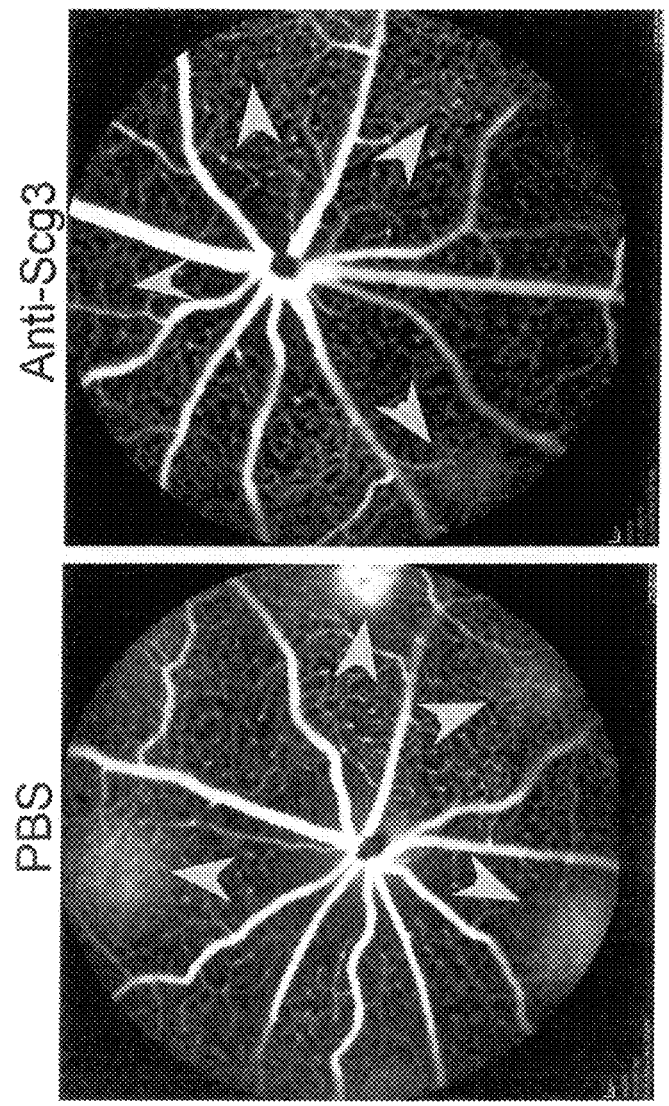
FIG. 10 shows that anti-Scg3 therapy ameliorated choroidal neovascularization (CNV). CNV was induced by laser photocoagulation (4 spots/eye). After 7 days, affinity-purified anti-Scg3 polyclonal antibody (0.36 µg/1 µl/eye) was intravitreally injected into one eye of CNV mice with PBS for the contralateral eye. CNV-related retinal vascular leakage was analyzed by fluorescein angiography at Day 14.
Figure 11:
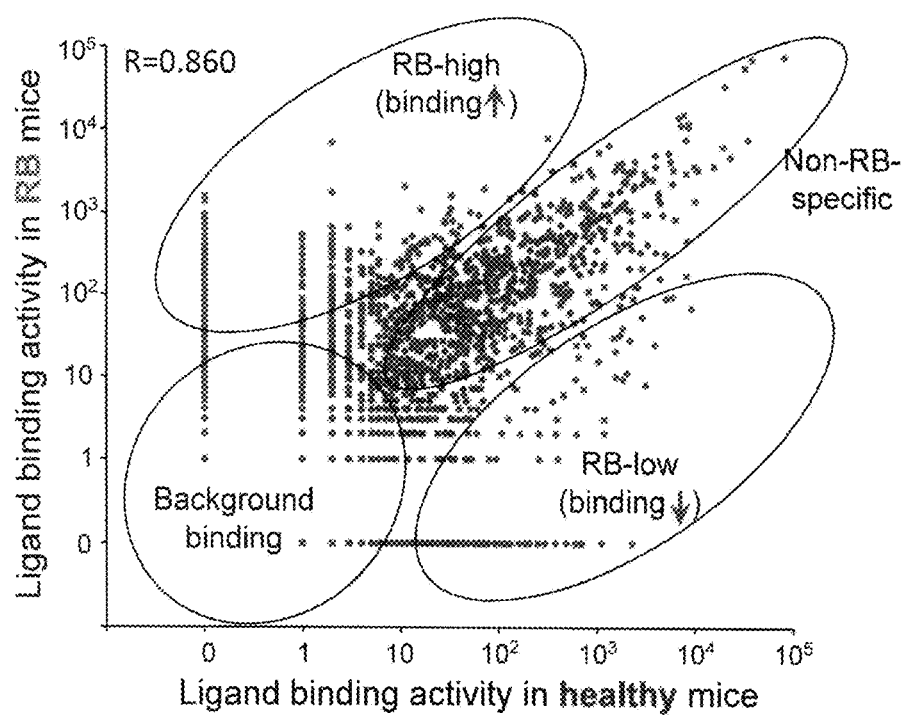
FIG. 11 is an actual graph of binding activity plot, showing systematic profiling of disease-specific endothelial ligands in retinoblastoma (RB) mice. Ligandomics was performed in RB and control mice, as described in FIG. 3. All identified ligands with binding activity to RB or retinal endothelium were quantitatively compared by binding activity plot to identify diabetes-specific ligands. Pearson correlation coefficient R=0.860.

Laser-induced CNV in animals has been widely used as a model for vascular AMD. C57BL/6 mice (~7-8 weeks old, male) were treated with laser photocoagulation to induce CNV, as described (Lambert et al., 2013, *Nat. Protoc.* 8:219702211). Briefly, diode laser photocoagulation (75-μm spot size, 0.1-sec duration, 110 mW) was performed on mouse retina. Four laser photocoagulation burns were delivered to each retina lateral to the optic disc, through a slit lamp, with a coverslip used as a contact lens. Only lesions with a subretinal bubble developed were used for experiments. After 7 days, affinity-purified anti-Scg3 polyclonal antibody (0.36 μg/1 μl/eye) or PBS was intravitreally injected into one eye of CNV mice with PBS for the contralateral eye. The retinal vascular leakage from CNV was analyzed at Day 14 by fluorescein angiography. Fluorescein sodium (2.5%, 0.1 ml) was intraperitoneally injected into mice. Fluorescein angiography was performed at 10 min post fluorescein injection. The results shows that anti-Scg3 antibody ameliorated CNV (FIG. 10), suggesting that Scg3 is a promising target for anti-angiogenesis therapy of wet AMD.

Example 2

Systematic Identification of Cancer-Related Endothelial Ligands

In another example to illustrate the embodiment of the invention, ligandomics was applied to cancer-bearing mice to systematically identify cancer-specific endothelial ligands in an in vivo setting.

Angiogenic factors play an important role in regulating blood supply to growing cancer. A number of angiogenesis factors and inhibitors have been identified. Several of them have been approved by FDA for anti-angiogenesis therapies of cancers, such as anti-VEGF therapy. Owing to technical difficulties, all endothelial ligands are traditionally identified and characterized for their cancer relevance on a case-by-case basis with technical challenges. As a result, it is unclear how many cancer-associated endothelial ligands are yet to be identified and which one is particularly relevant to a specific cancer. The knowledge gap hinders our capability to develop new ligand-based cancer therapy. Herein one of the embodiments (FIG. 3) was used to systematically identify cancer-associated endothelial ligands for rational design of novel ligand-based therapies.

In Vivo Binding Selection

Retinoblastoma (RB) is the most common intraocular tumor in children. Transgenic (Tg) mice expressing SV40 T antigen under the control of the promoter for β-unit of luteinizing hormone spontaneously develop RB (O'Brien et al., 1989, *Trans. Am. Ophthalmol. Soc.* 87:301-322). These mice were used as a cancer model for quantitative ligandomics to systematically identify cancer-associated ligands with therapeutic potentials.

Transgenic mice were identified by genotyping. RB in the Tg mice was verified by eye fundus exam at 8 weeks of age. In vivo binding selection was performed for the RB tissue in the Tg mice or the retina in the littermate controls (3 mice/group/round) at 16 weeks of age as in Example 1 (FIG. 3A). A total of three rounds of in vivo OPD selection were performed to enrich EC-binding ligands, which were identified by NGS. The copy numbers of the clones identified by NGS were the equivalent of their endothelial binding activities.

Quantitative Ligandomics Analysis

The results showed that a total of 703,279 and 725,793 valid sequence reads were identified by NGS for RB and control retina and matched to 1,857 and 1,137 ligands in NCBI CCDS database, respectively (Table 2). Quantitative comparison of all identified ligands between RB and control retina systematically identified RB-associated ligands, including 222 ligands with increased binding activity to RB ECs and 77 ligands with decreased binding (p<0.001, $\chi^2$ test) (Table 2).

TABLE 2

Retinoblastoma (RB)-associated endothelial ligands identified by quantitative ligandomics

| CCDS_ID | Protein | Binding activity | | Activity ratio |
| | | RB | Control | |
| --- | --- | --- | --- | --- |
| RB-high ligands with increased binding to RB ECs | | | | |
| CCDS23347.1 | Scg3* | 198 | 0 | 199.0 |
| CCDS40011.1 | Hdgfrp3* | 924 | 63 | 14.5 |
| Total identified sequences | | 703,279 | 725,793 | |
| Total identified ligands | | 1,857 | 1,137 | |
| Diabetes-related ligands* | | 667↑ | 171↓ | |

*p < 0.001,
RB versus control,
Chi-square ($\chi^2$) test.
3 mice/group/round.
All binding activities are normalized for quantitative data comparison.
Activity ratio = (RB + 1)/(Control + 1).

Quantitative comparison of the ligands in Table 1 and 2 revealed interesting similarities and differences between RB and DR. For example, both the diseases upregulated the binding of Scg3. Unlike RB with progressive angiogenesis for tumor growth, DR with EC apoptosis and acellular capillaries only develops late-onset angiogenesis. It is possible that reduced binding of HRP-3 in DR may exacerbate EC apoptosis, thereby delaying the onset of Scg3-induced angiogenesis. In contrast, increased binding of both Scg3 and HRP-3 in RB may contribute to progressive cancer angiogenesis, suggesting that the blockade of these two ligands may be beneficial to RB therapy but could have dichotomous effects on endothelial apoptosis and angiogenesis in DR. These data demonstrated that quantitative ligandomics enables systems biology analysis of RB-associated extrinsic regulations in a cell-wide context for in-depth understanding of cancer biology and discovery of therapeutic targets. This approach can be used to globally compare the ligandome profiles of different cancers to systematically delineate cancer-specific endothelial ligands in a ligandome scale. This method can also be used to globally compare the ligandome profiles of different stages of the same cancer to systematically delineate stage-specific endothelial ligands in a ligandome scale. Stage-specific angiogenic factors can be used as targets to develop stage-specific anti-angiogenesis therapies.

Rational Design of Anti-Angiogenesis Therapies

Anti-angiogenesis is an important therapeutic strategy for cancer. Scg3 may be a new angiogenic factor to preferentially promote angiogenesis in RB as well as many other cancers. Therefore, antibodies, including humanized monoclonal antibodies, or single-chain variable fragment antibodies (scFvs) against Scg3 may block its angiogenic activity for cancer therapy. Moreover, small molecules, peptides or nucleotide aptamer to block endothelial binding of Scg3 or HRP-3 may also be valuable strategies for anti-angiogenesis therapy of RB and other cancers. Scg3 is not angiogenically active in normal blood vessels (FIG. 8), but its receptor expression on tumor endothelium is upregulated (Table 2). Furthermore, Scg3 expression is upregulated in tumor cells (Wang et al., 2014, *Cancer Lett.* 352:169-178). These suggest that Scg3 is a promising target for anti-angiogenesis therapy of cancer.

Moreover, small molecules, peptides or nucleotide aptamer to neutralizing Scg3 functional binding and functional activity can be used for anti-angiogenesis therapy of diabetic macular edema, proliferative diabetic retinopathy, AMD, and cancers. Alternatively, small interfering RNA (siRNA), small hairpin RNA (shRNA) or microRNA (miRNA) can also be used to specifically silence Scg3 for anti-angiogenesis therapy of diabetic macular edema, proliferative diabetic retinopathy, AMD, and cancers. Scg3 can be used as angiogenic factor to treat ischemic diseases, such as diabetic foot.

What is claimed is:

1. A method of treating diabetic retinopathy in a subject in need thereof comprising administering a therapeutically effective amount of a secretogranin III (Scg3) inhibitor that specifically blocks the angiogenic or vascular leakage activity of Scg3.

2. The method of claim 1, wherein the Scg3 inhibitor for anti-angiogenesis therapy comprises Scg3-blocking antibodies, single-chain variable fragment antibodies, peptides, small molecules or nucleotide aptamers.

* * * * *